(12) United States Patent
Martin et al.

(10) Patent No.: US 6,806,070 B1
(45) Date of Patent: Oct. 19, 2004

(54) USE OF BACTERIAL EXTRACTS OF THE PSEUDOMONADACEAE FAMILY AS COSMETIC AGENTS

(75) Inventors: Richard Martin, Rochecorbon (FR); Pascal Hilaire, Vouvray (FR); Nathalie Pineau, Poitiers (FR); Lionel Breton, Versailles (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/049,552

(22) PCT Filed: Aug. 26, 1999

(86) PCT No.: PCT/FR99/02043

§ 371 (c)(1),
(2), (4) Date: Apr. 18, 2002

(87) PCT Pub. No.: WO01/13878

PCT Pub. Date: Mar. 1, 2001

(51) Int. Cl.[7] .............................. C12P 1/04; C12P 13/20; A61K 38/00; C07K 1/00
(52) U.S. Cl. ................. 435/170; 424/93.47; 424/94.62; 424/94.64; 424/94.65; 424/94.66; 435/109; 435/131; 435/194; 435/825; 435/849; 435/874; 514/12; 530/866; 530/867
(58) Field of Search .............................. 424/93.47, 94.2, 424/94.62, 94.64, 94.65, 94.66; 435/109, 131, 170, 194, 825, 849, 874; 514/12; 530/866, 867

(56) References Cited

U.S. PATENT DOCUMENTS

| | | | |
|---|---|---|---|
| 5,086,040 A | | 2/1992 | Bonfils et al. |
| 5,653,982 A | * | 8/1997 | Spagnoli et al. ............ 424/401 |
| 5,856,451 A | | 1/1999 | Olsen et al. |

FOREIGN PATENT DOCUMENTS

| | | |
|---|---|---|
| DE | 196 28 454 A1 | 1/1998 |
| DE | 198 24 073 A1 | 12/1999 |
| EP | 0 404 660 A2 | 12/1990 |
| EP | 0 404 661 A2 | 12/1990 |
| EP | 0 631 773 A1 | 1/1995 |
| FR | 2 775 186 A1 | 8/1999 |
| JP | 3-275610 A2 | 12/1991 |
| JP | 8-003018 A2 | 1/1996 |
| JP | 8-208427 A2 | 8/1996 |

OTHER PUBLICATIONS

Spraycar, M. (Editor),Stedman's Medical Dictionary. 1995. Williams and Wilkins, Baltimore, p. 1575.*

* cited by examiner

*Primary Examiner*—Christopher R. Tate
*Assistant Examiner*—Kailash C. Srivastava
(74) *Attorney, Agent, or Firm*—Oliff & Berridge, PLC

(57) ABSTRACT

Use of an extract of bacterium from the family Pseudomonadaceae in the production of cosmetic compositions in particular for combating ageing of the skin.

33 Claims, No Drawings

USE OF BACTERIAL EXTRACTS OF THE PSEUDOMONADACEAE FAMILY AS COSMETIC AGENTS

The invention relates to the use of extracts of bacteria from the family Pseudomonadaceae, as cosmetic agents for in particular combating ageing of the skin in humans.

It is known that ageing of the skin manifests itself, firstly, through a decrease in the number and a fragmentation of the elastic fibres of the dermis. Elastin becomes more sensitive to lysis by elastase and the deterioration of the elastin leads to disorganization of the elastic fibres. These phenomena result in a loss of the elasticity of the skin and in the formation of wrinkles.

Another manifestation of ageing of the skin is dryness of the skin, which becomes rough, with a loss of flexibility of the epidermis and a tendency towards desquamation. In the connective tissue of the skin of young individuals, the high content of hyaluronates, which are highly hydrophilic, promotes moisturization of the dermis, which is an essential element of skin tonicity. During ageing, the hyaluronate content, and therefore the water content, of the dermis greatly decreases, with the unfortunate consequences that the skin is flaccid and there is less diffusion of dermal water to the epidermis, which dries out. In addition, as a consequence of the decrease in the water content of the dermis, the circulation of metabolites, of ions and of oxygen is in particular impeded and, therefore, the metabolism of the dermal and epidermal cells slows down. The decrease in the hyaluronate content is linked to the activity of an enzyme, hyaluronidase, which cleaves the glycosidic bonds of hyaluronates. For this reason, this enzyme plays a very important role in ageing of the skin.

In addition, the drying out of the epidermis decreases the gaseous exchanges with the ambient atmosphere at the surface of the skin. This phenomenon of gaseous exchange, called cutaneous respiration, decreases with age.

Moreover, it is known that exposure to sunlight may cause an inflammatory reaction in skin tissue and that, after repeated and prolonged exposure to sunlight, in particular to UVA radiation, the skin eventually becomes dried out, excessively wrinkled and lacking in flexibility: this premature ageing of the skin is called "photoageing".

It is therefore desirable to find new means in particular for protecting the skin against accelerated or premature ageing, and for more effectively protecting the skin against damage caused by exposure to sunlight, including against photoageing of the skin.

It has now been discovered that extracts of bacteria from the family Pseudomonadaceae, and in particular bacteria of the genus Pseudomonas, when applied to the skin, are in particular capable of improving moisturization of the skin and protecting the skin against certain harmful consequences of inflammatory reactions subsequent to exposure to ultraviolet radiation. More generally, they are capable of decreasing and/or delaying ageing of the skin, including photoageing of the skin.

These bacterial extracts have in particular the property of inhibiting lesions of the connective tissue of the skin subsequent in particular to UV exposure. These bacterial extracts in fact have the property of inhibiting elastase release in areas of inflammation, as shown in the experimental section hereinafter, and they also have the property of inhibiting elastase activity. More generally, these bacterial extracts, when applied to the skin, have anti-inflammatory and soothing properties, and improve the appearance of skin which exhibits a local inflammation or micro-inflammations, including after exposure to sunlight.

These bacterial extracts also have an inhibitory effect on hyaluronidase activity. Thus, they make it possible to prevent or treat dryness of the skin, including after exposure to sunlight and in cases of natural or premature ageing of the skin, and also in cases of photoageing. In addition, they improve skin tonicity by promoting moisturization of the dermis.

A subject of the invention is therefore the use of an extract of at least one bacterium from the family Pseudomonadaceae, as a cosmetic agent for combating natural or premature ageing of the skin, including photoageing, for improving the appearance and tonicity of dry skin, for preserving or improving skin elasticity, and/or for improving the appearance of skin which exhibits an inflammatory reaction, including after exposure to sunlight. In the present application, the expression "combating" ageing of the skin means preventing delaying, or even treating, ageing of the skin.

Among the bacteria which may be used according to the invention, mention may be made in particular of:

Pseudomonas vesicularis, one of the types of which is the strain deposited at the ATCC under the No. 11426.

Pseudomonas maltophilia, one of the types of which is the strain deposited at the ATCC under the No. 13637.

Pseudomonas maltophilia is also called Stenotrophomonas maltophilia.

In the present application, the expression "extracts of bacteria" or "bacterial extracts" denotes both the biomasses obtained after culturing the bacteria and the products obtained from these biomasses, in particular after purification and/or sterilization and/or fractionation. For example, the biomasses may optionally be at least partially dehydrated and/or ground. They may be sterilized, for example by heating. Of course, the invention extends to the use of extracts comprising any fraction of the biomass which has the same anti-ageing of the skin properties as the whole biomass, and in particular fractions which inhibit elastase secretion in areas of inflammation and/or which inhibit hyaluronidase activity. In the present application, the notion of extracts also encompasses derivatives obtained by chemical modification of certain functional groups (amines for example).

The method for preparing a bacterial extract used according to the invention comprises the steps consisting in culturing, in vitro, the bacteria according to known methods and then in collecting the biomass obtained.

Bacteria of the family Pseudomonadaceae are strictly aerobic Gram-negative bacteria. They grow on ordinary nutrient media, for example at temperatures of the order of 25 to 30° C.

To separate and isolate the biomass, various known methods, such as filtration or centrifugation, may be used. It is also possible to dry the biomass and concentrate it by dehydration, in particular by heating under reduced pressure (for example at a temperature of the order of approximately 80 to 120° C.) or by lyophilization.

The bacterial extracts may be used in the form of derivatives, for example of at least partially acylated derivatives. The acylation is carried out using a carboxylic acid anhydride or with a corresponding acid chloride. Use may be made, for example, of acetic anhydride or acetyl chloride. The acylation reaction is carried out such that at least some of the primary and secondary amine groups present in the bacterial biomass are acylated. The proportions of acylating agents and the acylation reaction conditions are easily determined by assaying, according to conventional methods, the primary and secondary amine groups before and after the acylation reaction.

The extracts of Pseudomonadaceae, or derivatives thereof, are introduced, as active ingredients, into compositions intended to be applied to the skin and/or to the scalp. These compositions exhibit good skin tolerance.

The invention therefore relates to a cosmetic composition comprising, as an active ingredient, an extract of at least one bacterium from the family Pseudomonadaceae, in combination with an excipient which is acceptable in cosmetology.

The excipients present in the composition of the invention are usual excipients. They are excipients which are compatible with use on the skin, on the scalp and/or on the hair.

In the compositions used according to the invention, the bacterial extracts are generally present in a proportion of 0.0005% to 5%, for example of 0.001% to 2%, and in particular of 0.01% to 2%, by weight of bacterial solids, relative to the: weight of the composition.

These compositions may contain the bacterial extract in the form of dispersions (in particular emulsions) in a suitable vehicle, such as for example water, organic solvents, fatty substances including oils, and mixtures thereof.

The compositions may in particular be in the form of water/alcohol or oil/alcohol lotions, of gels, of emulsions with a liquid consistency, of creams, of solid sticks or of vesicular dispersions. These compositions may be prepared according to the usual methods. They contain the ingredients and vehicles which make it possible to provide them in particular in one of the forms which have just been mentioned. They may contain, besides the bacterial extracts, other active ingredients, such as for example substances which absorb ultraviolet, conventional moisturizers, free-radical scavengers, antioxidants, thermal spring water, such as the water from the thermal springs of La Roche-Posay, emollients or other usual ingredients, such as preserving agents, fragrances, etc. Such ingredients, and also the use thereof, are known and will not be described further here.

The thermal spring water optionally used in the composition of the invention is in particular thermal spring water which has cosmetic properties beneficial for the skin. For example, La Roche-Posay (France) thermal spring water, which is rich in selenium, in particular has protective properties against the deleterious effects of UVA radiation on the skin, and also has antioxidant properties which promote the survival of fibroblasts exposed to UVB radiation. La Roche-Posay thermal spring water therefore constitutes an advantageous active ingredient, in particular in the cosmetic products intended to be used during or after exposure of the skin to sunlight.

A subject of the invention is also a cosmetic treatment method for combating ageing of the skin, characterized in that a composition as defined above is applied to the skin or to the scalp. This composition is applied according to the usual methods.

The following examples illustrate the invention. In these examples, the percentages are percentages by weight.

EXAMPLES

Example 1

Culturing *Pseudomonas vesicularis* and *Pseudomonas maltophilia*

The *Pseudomonas vesicularis* strain cultured was obtained from the ATCC (ATCC 11426).

The *Pseudomonas maltophilia* strain is the ATCC 13637 strain.

The bacteria are cultured in Difco Nutrient Broth 003 culture medium(Medium 3 ATCC). The pH of the medium is adjusted to 7.15 before sterilization at 121° C. for at least 20 minutes.

The culturing is carried out at 26° C. with shaking (100 rpm), ensuring a dissolved oxygen content at least equal to 15%.

After culturing for 24 hours, the biomass is harvested by centrifugation.

The biomass may be stabilized by heating in an autoclave, lyophilized, frozen and/or ground.

It is also possible, if desired, to acetylate the primary and secondary amine groups, totally or partially, via the action of acetic anhydride.

Example 2

Cream

This cream corresponds to the following composition:

Lyophilizate based on *Ps. vesicularis* obtained according to Example 1 . . . 0.05%

Carbomer 940* . . . 0.30%

Triethanolamine . . . 0.30%

Stearic acid . . . 3.00%

Cetyl alcohol . . . 2.00%

Self-emulsifiable glycerol monostearate . . . 3.00%

Soya bean oil . . . 10.00%

Lanolin alcohol . . . 2.00%

Isopropyl myristate . . . 4.00%

Cetearyl 2-ethylhexanoate . . . 4.00%

Perhydrosqualene . . . 3.00%

Paraffin . . . 2.00%

Glycerol . . . 3.00%

Preserving agents . . . 0.30%

La Roche-Posay thermal spring water** . . . 15.00%

Purified water, q.s. for . . . 100.00%

Carbomer 940: commercial brand denoting a crosslinked polyacrylic acid
La Roche-Posay spa centre (France)

The lyophilizate based on *Pseudomonas vesicularis* may be replaced with a lyophilizate based on *Pseudomonas maltophilia*.

In a similar manner, a cream containing 0.01% of *Pseudomonas vesicularis* lyophilizate and 0.05% of *Pseudomonas maltophilia* lyophilizate was prepared.

To prepare this cream, the aqueous phase containing the glycerol, the preserving agents and the water is heated to 80° C.; the Carbomer 940 is dispersed therein, followed by neutralization with triethanolamine. The fatty phase, heated and homogenized at 80° C., is introduced into the aqueous phase, with vigorous stirring. The lyophilizate of Example 1 is dispersed in 10 g of water and introduced, at 40° C., into the cream with stirring. The entire mixture is cooled to ambient temperature.

This cream is applied to the skin of the face and of the neck once or twice a day. It improves the appearance of dry skin. It also makes it possible to improve skin tonicity.

Example 3

Milk for the Skin

This milk has the following composition:

Lyophilizate of *Ps. vesicularis* obtained according to Example 1 . . . 0.10%

Self-emulsifiable glyceryl monostearate . . . 3.00%

Petroleum-jelly . . . 1.50%

Liquid petroleum jelly . . . 2.50%

Rice bran oil . . . 1.50%

Volatile silicone oil . . . 5.00%

Karite butter . . . 3.00%

Carbomer 940 . . . 0.20%
Triethanolamine . . . 0.20%
Xanthan gum . . . 0.10%
Glycerol . . . 3.00%
Fragrance . . . 0.10%
Preserving agents . . . 0.30%
Water, q.s. for . . . 100.00%

This milk is prepared in a similar way to that described in Example 2.

When applied to the skin after exposure to sunlight, it has soothing properties.

When applied to the skin of the face, this milk decreases the effect of accelerated ageing of the skin observed in particular in individuals who are repeatedly exposed to sunlight.

Example 4
Cream

An emulsion having the following composition was prepared according to the same procedure as in Example 2:

Lyophilizate of Ps. vesicularis obtained according to Example 1 . . . 0.10%
Self-emulsifiable base . . . 20.00%
Codex liquid petroleum jelly . . . 5.00%
Glycerol . . . 5.00%
Aluminium stearate . . . 0.50%
Dipotassium EDTA . . . 0.05%
Magnesium sulphate . . . 0.70%
Preserving agents . . . 20%
Antioxidants . . . 0.05%
Fragrance . . . 0.30%
Water, q.s. for . . . 100.00%

In the above formulation, the Pseudomonas vesicularis lyophilizate may be replaced with a Pseudomonas maltophilia lyophilizate. A mixture of the two lyophilizates may also be used.

The self-emulsifiable base comprises:
Mineral oil
Codex petroleum jelly
Ozokerite
Glyceryl oleate
Liquid lanolin.

This cream, when applied to the skin, makes it possible to decrease the effects of ageing of the skin and/or of photo-ageing of the skin. It also makes it possible to improve the degree of moisturization of the skin of elderly individuals.

Example 5
Antisun Emulsion

This emulsion makes it possible to protect the skin against ultraviolet rays. It corresponds to the following formula:

Lyophilizate of Example 1 . . . 1.00%
Stearic acid . . . 3.00%
Cetyl alcohol . . . 1.50%
Self-emulsifiable glyceryl monostearate . . . 3.00%
Sunflower oil . . . 8.00%
Polyacrylamide . . . 3.00%
Octyl methoxycinnamate . . . 4.00%
Triethanolamine salt of benzene-1,4-di-(3-methylidene)-10-camphosulphonic acid (Mexoryl SX) . . . 2.60%
Glycerol . . . 5.00%
Tocopherol . . . 2.00%
Preserving agents . . . 0.30%
Ethylenediaminetetramethylene phosphonate (pentasodium salt) . . . 0.10%
Purified water, q.s. for . . . 100.00%

Example 6
Elastase Inhibition Test

The test is carried out using elastase isolated from human leukocytes.

The test is performed according to the method described by E. O. Adeyemi et al., J. Pharm. Pharmacol., 42:487–490 (1990). The tests are carried out with a lyophilizate obtained as described in Example 1.

The lyophilizate originating from the Pseudomonas maltophilia culture, at a concentration of 0.05 g/l, decreases the elastase actiyity by 36%. At a concentration of 0.1 g/l, the lyophilizate originating from the Pseudomonas vesicularis culture decreases the elastase activity by 33% and the lyophilizate originating from a Pseudomonas maltophilia culture decreases the elastase activity by 53%.

Example 7
Inhibitory Effect on Hyaluronidase Activity

The test is carried out according to the conventional method described in Worthington Enzyme Manual, Enzymes and related biochemicals, Worthington Biochemical Corps., Frehold, N. J. 07728, USA (1993).

The bacterial lyophilizate studied is a Pseudomonas vesicularis lyophilizate. It is dissolved in 0.1 M phosphate bufffer, pH 5.3.

The reagents used are hyaluronic acid (Sigma H-1876) and Sigma hyaluronidase type IV-S (H-3884). The hyaluronic acid and hyaluronidase are mixed in phosphate buffer so as to obtain a solution containing 0.6 g/l of hyaluronic acid and 0.25 g/l of hyaluronidase.

The mixture is left to incubate for 15 minutes at 37° C.

A solution of bovine albumin at 1% in a 0.5 M acetate buffer, pH 4.2, is then added so as to precipitate the hyaluronic acid.

The amount of nondegraded hyaluronic acid is then measured by measuring light absorption at a wavelength of 540 nm.

The Pseudomonas vesicularis lyophilizate, at a concentration of 0.1%, inhibits the hyaluronidase activity by 30%.

What is claimed is:

1. A cosmetic treatment method applied to combat ageing of skin comprising a step of applying, to the skin or to the scalp, a composition comprising a biomass obtained from a culture of at least one bacterium selected from the group consisting of Pseudomonas vesicularis and Pseudomonas maltophilia,
   wherein said biomass is obtained by culturing said at least one in a culture medium bacterium and separating the biomass from the culture medium and optionally at least partially dehydrating, sterilizing, purifying, grinding and/or acylating the separated biomass.

2. The method according to claim 1, wherein said biomass is purified and/or ground and/or partially or completely dehydrated and/or sterilized.

3. The method according to claim 1, said composition containing the biomass in a proportion of 0.0005% to 5% by weight of biomass solids relative to the total weight of the composition.

4. The method according to claim 1, wherein said ageing is photoageing.

5. The method according to claim 1, wherein said separating is by filtration and/or centrifugation.

6. The method according to claim 1, wherein said dehydrating is by heating and/or lyophilization.

7. The method according to claim 1, wherein said sterilizing is by heating.

8. A cosmetic treatment method applied to improve appearance and tonicity of dry skin comprising a step of applying, to the skin or to the scalp, a composition comprising a biomass obtained from a culture of at least one bacterium selected from the group consisting of *Pseudomonas vesicularis* and *Pseudomonas maltophilia*, wherein said biomass is obtained by culturing said at least one in a culture medium bacterium and separating the biomass from the culture medium and optionally at least partially dehydrating, sterilizing, purifying, grinding and/or acylating the separated biomass.

9. The method according to claim 8, wherein said biomass is purified and/or ground and/or partially or completely dehydrated and/or sterilized.

10. The method according to claim 8, said composition containing the biomass in a proportion of 0.0005% to 5% by weight of biomass solids relative to the total weight of the composition.

11. The method according to claim 8, wherein said separating is by filtration and/or centrifugation.

12. The method according to claim 8, wherein said dehydrating is by heating and/or lyophilization.

13. The method according to claim 8, wherein said sterilizing is by heating.

14. A cosmetic treatment method applied to preserve or improve skin elasticity comprising a step of applying, to the skin or to the scalp, a composition comprising a biomass obtained from a culture of at least one bacterium selected from the group consisting of *Pseudomonas vesicularis* and *Pseudomonas maltophilia*, wherein said biomass is obtained by culturing said at least one in a culture medium bacterium and separating the biomass from the culture medium and optionally at least partially dehydrating, sterilizing, purifying, grinding and/or acylating the separated biomass.

15. The method according to claim 14, wherein said biomass is purified and/or ground and/or partially or completely dehydrated and/or sterilized.

16. The method according to claim 14, said composition containing the biomass in a proportion of 0.0005% to 5% by weight of biomass solids relative to the total weight of the composition.

17. The method according to claim 14, wherein said separating is by filtration and/or centrifugation.

18. The method according to claim 14, wherein said dehydrating is by heating and/or lyophilization.

19. The method according to claim 14, wherein said sterilizing is by heating.

20. A cosmetic treatment method applied to improve appearance of skin which exhibits a local inflammatory reaction comprising a step of applying, to the skin or to the scalp, a composition comprising a biomass obtained from a culture of at least one bacterium selected from the group consisting of *Pseudomonas vesicularis* and *Pseudomonas maltophilia*, wherein said biomass is obtained by culturing said at least one in a culture medium bacterium and separating the biomass from the culture medium and optionally at least partially dehydrating, sterilizing, purifying, grinding and/or acylating the separated biomass.

21. The method according to claim 20, wherein said biomass is purified and/or ground and/or partially or completely dehydrated and/or sterilized.

22. The method according to claim 20, said composition containing the biomass in a proportion of 0.0005% to 5% by weight of biomass solids relative to the total weight of the composition.

23. The method according to claim 20, wherein said separating is by filtration and/or centrifugation.

24. The method according to claim 20, wherein said dehydrating is by heating and/or lyophilization.

25. The method according to claim 20, wherein said sterilizing is by heating.

26. A cosmetic composition comprising, as an active ingredient, a biomass obtained from a culture of at least one bacterium selected from the group consisting of *Pseudomonas vesicularis* and *Pseudomonas maltophilia*, in combination with an excipient that is acceptable in cosmetology, wherein said biomass is obtained by culturing said at least one in a culture medium bacterium and separating the biomass from the culture medium and optionally at least partially dehydrating, sterilizing, purifying, grinding and/or acylating the separated biomass.

27. The composition according to claim 26, wherein said biomass is purified and/or ground and/or partially or completely dehydrated and/or sterilized.

28. The composition according to claim 26, wherein said biomass is at least partially dehydrated.

29. The composition according to claim 26, wherein said biomass is present in a proportion of 0.0005% to 5% by weight of biomass solids relative to the total weight of the composition.

30. The composition according to claim 29, wherein said proportion is within the range of 0.0001% to 2% by weight.

31. The composition according to claim 26, wherein said separating is by filtration and/or centrifugation.

32. The composition according to claim 26, wherein said dehydrating is by heating and/or lyophilization.

33. The composition according to claim 26, wherein said sterilizing is by heating.

* * * * *